US008389537B2

(12) United States Patent
Manley et al.

(10) Patent No.: US 8,389,537 B2
(45) Date of Patent: Mar. 5, 2013

(54) SALTS OF 4-METHYL
N-[3-(4-METHYL-IMIDAZOL-1-YL)-5-
TRIFLUOROMETHYL-PHENYL]-3-
(4-PYRIDIN-3-YL-PYRIMIDIN-2-YLAMINO)-
BENZAMIDE

(75) Inventors: Paul W Manley, Arlesheim (CH);
Wen-Chung Shieh, Berkeley Heights,
NJ (US); Paul Allen Sutton, Parsippany,
NJ (US); Piotr H Karpinski, Lincoln
Park, NJ (US); Raeann Wu, Pine Brook,
NJ (US); Stéphanie Monnier,
Raedersheim (FR); Jörg Brozio, Basel
(CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/419,132

(22) Filed: Mar. 13, 2012

(65) Prior Publication Data
US 2012/0270891 A1 Oct. 25, 2012

Related U.S. Application Data

(62) Division of application No. 11/995,898, filed as application No. PCT/US2006/027878 on Jul. 18, 2006, now Pat. No. 8,163,904.

(60) Provisional application No. 60/701,406, filed on Jul. 20, 2005, provisional application No. 60/716,213, filed on Sep. 12, 2005.

(51) Int. Cl.
*A61K 31/506* (2006.01)
*A61P 35/00* (2006.01)
*C07D 401/14* (2006.01)

(52) U.S. Cl. ........................ 514/275; 544/331
(58) Field of Classification Search .................. 544/331; 514/275
See application file for complete search history.

(56) References Cited

U.S. PATENT DOCUMENTS

| 5,516,775 A | 5/1996 | Zimmermann et al. |
| 7,169,791 B2 | 1/2007 | Breitenstein et al. |
| 8,163,904 B2 * | 4/2012 | Manley et al. ............... 544/331 |

FOREIGN PATENT DOCUMENTS

| EP | 0 588 762 A | 3/1994 |
| WO | WO 95 09853 A | 4/1995 |
| WO | WO 2004/005281 | 1/2004 |

OTHER PUBLICATIONS

Zimmermann J et al: "Potent and selective inhibitors of the Abl-kinase: phenylamino-pyrymidine (PAP) derivatives", Bioorganic & Medicinal Chemistry Letters, Oxford, GB, vol. 7, No. 2, Jan. 21, 1997, pp. 187-192.
Zimmermann J et al: "Phenylamino-pyrimidine (PAP)—derivatives: a new class of potent and highly selective PDGF-receptor autophosphorylation inhibitors", Bioorganic & Medicinal Chemistry Letters, Oxford, GB, vol. 6, No. 11, Jun. 4, 1996, pp. 1221-1226.
Paul R et al., "Preparation of substituted N-phenyl-4-aryl-2-pyrimidinamines as mediator release inhibitors", Journal of Medicinal Chemistry, American Chemical Socity, Washington, US, vol. 36, No. 19, Sep. 17, 1993, pp. 2716-2725.
Mass, R.D., Int. J. Radiation Oncology Bio. Phys., vol. 58(3): 932-940, 2004.
Fabbro et al., Pharmacology & Therapeutics, 93, 79-98, 2002.
Cohen et al., Current Opinion in Chemical Biology, 3, 459-465, 1999.
Freshney et al., Culture of Animal Cells, A Manual of Basic Technique, Alan R. Liss, Inc., 1983, New York, pp. 4.
Dermer et al., Bio/Tecnology, 1994, 12:320.
Powell et al., British Journal of Dermatology, 141: 802-810, 1999.
Golub et al., Science, 286, 531-537, 1999.
Cecil Textbook of Medicine, edited by Bennet, J.C., and Plum F., 20th edition, vol. 1, 1004-1010, 1996.

* cited by examiner

*Primary Examiner* — Venkataraman Balasubramanian
(74) *Attorney, Agent, or Firm* — Stephen Johnson

(57) ABSTRACT

Salts of 4-methyl-N-[3-(4-methyl-imidazol-1-yl)-5-trifluoromethyl-phenyl]-3-(4-pyridin-3-yl-pyrimidin-2-ylamino)-benzamide are prepared by various processes.

2 Claims, 8 Drawing Sheets

SALTS OF 4-METHYL N-[3-(4-METHYL-IMIDAZOL-1-YL)-5-TRIFLUOROMETHYL-PHENYL]-3-(4-PYRIDIN-3-YL-PYRIMIDIN-2-YLAMINO)-BENZAMIDE

This application is a divisional of U.S. application Ser. No. 11/995,898, which is a national Stage entry of PCT/US2006/027878 filed Jul. 18, 2006, which claims benefit of U.S. Provisional Application No. 60/701,406, filed Jul. 20, 2005, and U.S. Provisional Application No. 60/716,213, filed Sep. 12, 2005, which in their entirety are herein incorporated by reference.

BACKGROUND OF THE INVENTION

1. Field of the Invention

This invention relates to salts of 4-methyl-N-[3-(4-methyl-imidazol-1-yl)-5-trifluoromethyl-phenyl]-3-(4-pyridin-3-yl-pyrimidin-2-ylamino)-benzamide, as well as to methods of making the same, pharmaceutical compositions comprising the same and methods of treatment using the same.

2. Related Background Art

The compound 4-methyl-N-[3-(4-methyl-imidazol-1-yl)-5-trifluoromethyl-phenyl]-3-(4-pyridin-3-yl-pyrimidin-2-ylamino)-benzamide of the formula

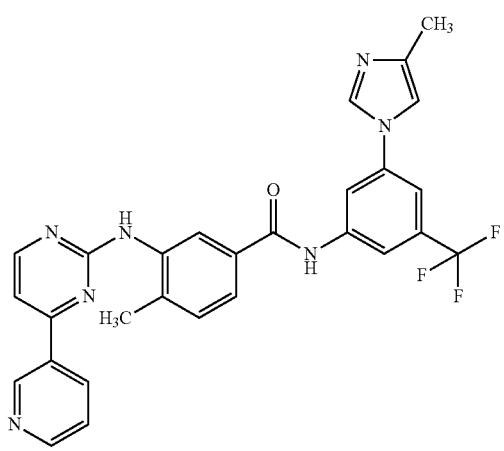 [SMILES: Cc1cn(-c2cc(NC(=O)c3ccc(C)c(Nc4nccc(-c5cccnc5)n4)c3)cc(C(F)(F)F)c2)cn1]

is described in WO 2004/005281 A1. Valuable pharmacological properties are attributed to this compound; thus, it can be used, for example, as a protein kinase inhibitor useful in therapy for diseases which respond to inhibition of protein kinase activity. WO 2004/005281 A1 does not disclose any specific salts or salt hydrates or solvates of 4-methyl-N-[3-(4-methyl-imidazol-1-yl)-5-trifluoromethyl-phenyl]-3-(4-pyridin-3-yl-pyrimidin-2-ylamino)-benzamide.

SUMMARY OF THE INVENTION

The present invention is directed to salts of 4-methyl-N-[3-(4-methyl-imidazol-1-yl)-5-trifluoromethyl-phenyl]-3-(4-pyridin-3-yl-pyrimidin-2-ylamino)-benzamide. Preferred embodiments of the present invention are directed to the hydrochloride, monophosphate, diphosphate, sulfate, methane sulfonate, ethane sulfonate, benzene sulfonate and p-toluene sulfonate salts of 4-methyl-N-[3-(4-methyl-imidazol-1-yl)-5-trifluoromethyl-phenyl]-3-(4-pyridin-3-yl-pyrimidin-2-ylamino)-benzamide.

The present invention is further directed to a method of preparing a variety of crystalline salts of 4-methyl-N-[3-(4-methyl-imidazol-1-yl)-5-trifluoromethyl-phenyl]-3-(4-pyridin-3-yl-pyrimidin-2-ylamino)-benzamide comprising the step of: reacting 4-methyl-N-[3-(4-methyl-imidazol-1-yl)-5-trifluoromethyl-phenyl]-3-(4-pyridin-3-yl-pyrimidin-2-ylamino)-benzamide free base with an acid of formula HB in a solvent.

The invention is further directed to pharmaceutical compositions comprising:
(a) a therapeutically effective amount of a salt of 4-methyl-N-[3-(4-methyl-imidazol-1-yl)-5-trifluoromethyl-phenyl]-3-(4-pyridin-3-yl-pyrimidin-2-ylamino)-benzamide; and
(b) at least one pharmaceutically acceptable carrier, diluent, vehicle or excipient.

The present invention is also directed to a method of treating a disease which responds to an inhibition of protein kinase activity comprising the step of administering to a subject in need of such treatment a therapeutically effective amount of a salt of 4-methyl-N-[3-(4-methyl-imidazol-1-yl)-5-trifluoromethyl-phenyl]-3-(4-pyridin-3-yl-pyrimidin-2-ylamino)-benzamide.

DETAILED DESCRIPTION OF THE INVENTION

The present invention is directed to salts of 4-methyl-N-[3-(4-methyl-imidazol-1-yl)-5-trifluoromethyl-phenyl]-3-(4-pyridin-3-yl-pyrimidin-2-ylamino)-benzamide; preferred embodiments of those salts are described below. Generally, as used herein, "salt" refers to a compound prepared by the reaction of an organic acid or base drug with a pharmaceutically acceptable mineral or organic acid or base; as used herein, "salt" includes hydrates and solvates of salts made in accordance with this invention. Exemplary pharmaceutically acceptable mineral or organic acids or bases are as listed in Tables 1-8 in *Handbook of Pharmaceutical Salts*, P. H. Stahl and C. G. Wermuth (eds.), VHCA, Zurich, pp. 334-345 (2002). As used herein, "polymorph" refers to a distinct "crystal modification" or "polymorphic form" or "crystalline form", which differs from another with respect to x-ray powder diffraction pattern, physicochemical and/or pharmacokinetic properties, and thermodynamic stability. Co-pending U.S. Patent Application No. 60/701,405, filed concurrently herewith, addresses the various polymorphic forms of 4-methyl-N-[3-(4-methyl-imidazol-1-yl)-5-trifluoromethyl-phenyl]-3-(4-pyridin-3-yl-pyrimidin-2-ylamino)-benzamide and salts thereof; the disclosure of that co-pending application is incorporated in its entirety by reference herein.

Figure 1:
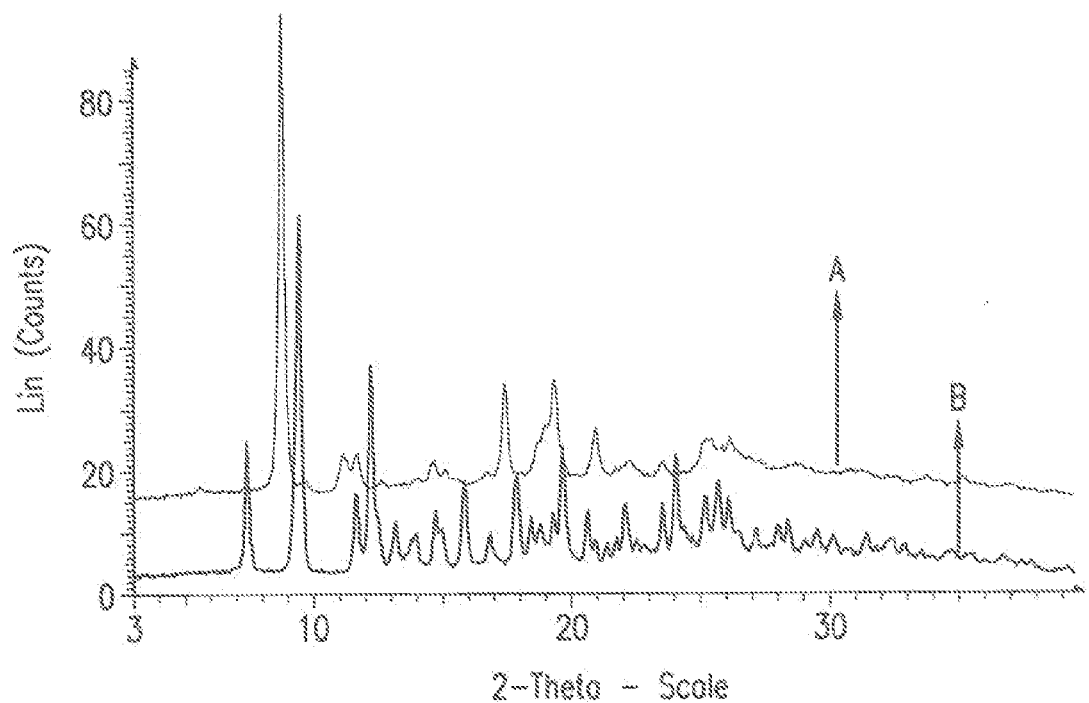
FIG. 1 shows the x-ray powder diffraction patterns (XR-PDs) for forms A and B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide.

The first embodiment of the present invention is directed to the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide. The hydrochloride salt (form B, monohydrate) is reproducibly produced from methanol when one equivalent hydrochloric acid is used. It is hygroscopic (when first tested, moisture uptake was up to 2% at 60% relative humidity and up to 2.7% at 95% relative humidity, though subsequent testing has shown even greater moisture uptake). It is very slightly soluble in water and slightly soluble in 0.1 N HCl, ethanol and 2-propanol. When tested with thermogravimetric analysis (TGA), two weight loss stages occur. The first stage (onset at about 80° C.) represents dehydration, and the second stage weight loss (at about 173° C.) represents the loss of HCl (decomposition). Its crystal structure ranges from good to excellent, it becomes amorphous upon grinding and it can withstand compression. The hydrochloride salt is stable at room temperature in standard equilibration tests. Other polymorphic forms of the hydrochloride salt, i.e., forms A, A', A", B', $S_B$, $S_B'$, C, C', $S_C$, D, and $S_E$, were also isolated. The XRPD pattern for forms A and B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide are shown in FIG. 1.

Figure 2:
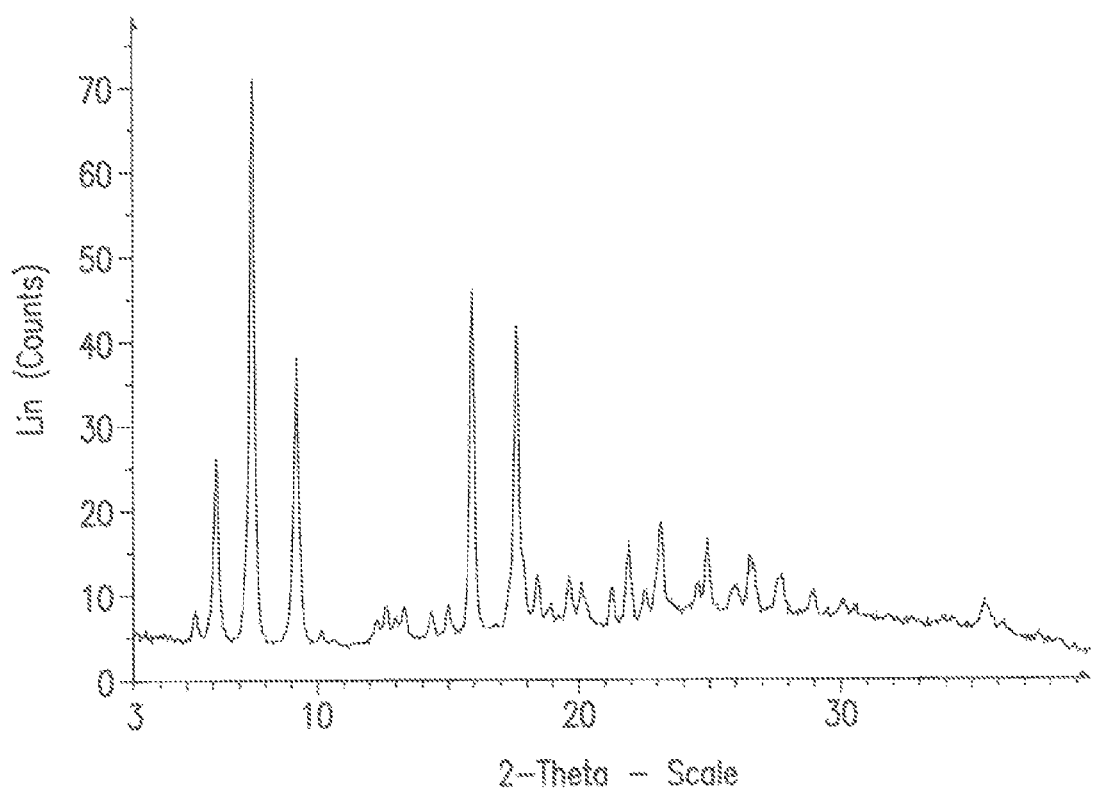
FIG. 2 shows the x-ray powder diffraction pattern (XRPD) for the monophosphate salt of 4-methyl-N-[3-(4-methyl-imidazol-1-yl)-5-trifluoromethyl-phenyl]-3-(4-pyridin-3-yl-pyrimidin-2-ylamino)-benzamide.

The second embodiment of the present invention is directed to the monophosphate salt of 4-methyl-N-[3-(4-methyl-imidazol-1-yl)-5-trifluoromethyl-phenyl]-3-(4-pyridin-3-yl-pyrimidin-2-ylamino)-benzamide. The $H_3PO_4$ mono-salt is reproducibly produced from methanol when one equivalent phosphoric acid is used. The weight loss (room temperature to 200° C.) is about 0.29%, and the sample melts at about 208° C. and decomposes at about 212° C. Its crystal structure is excellent. The XRPD pattern for the monophosphate salt of 4-methyl-N-[3-(4-methyl-imidazol-1-yl)-5-trifluoromethyl-phenyl]-3-(4-pyridin-3-yl-pyrimidin-2-ylamino)-benzamide is shown in FIG. 2.

Figure 3:
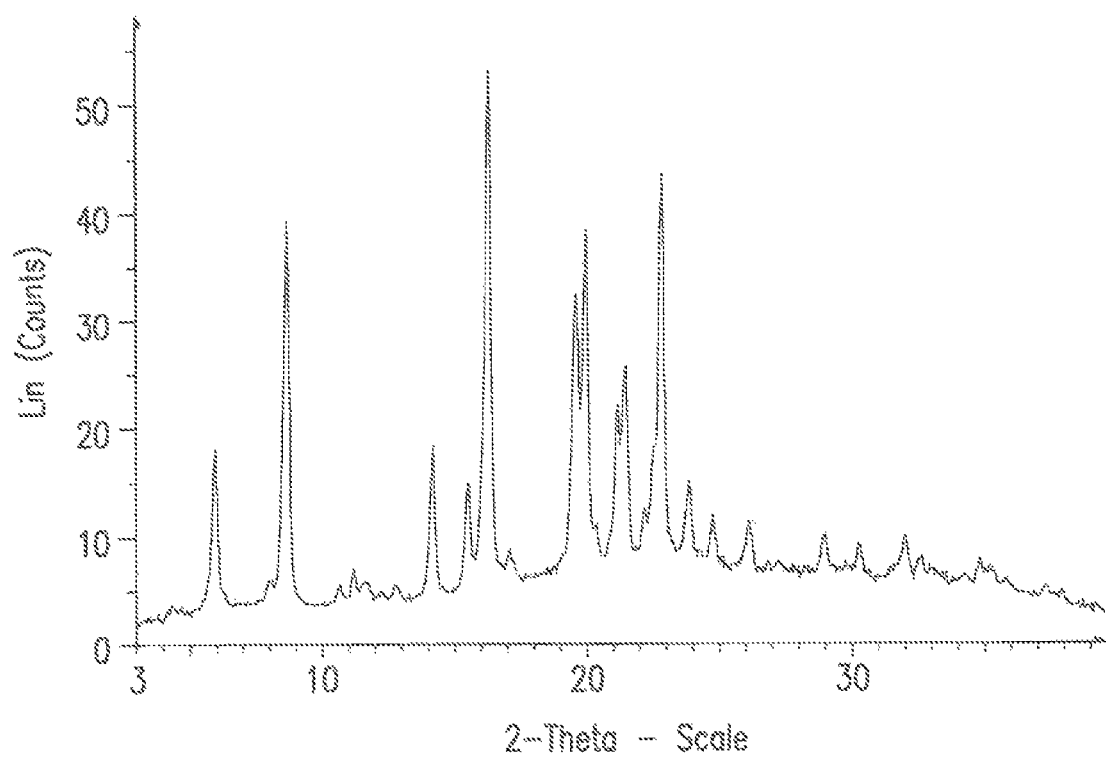
FIG. 3 shows the x-ray powder diffraction pattern for the diphosphate salt of 4-methyl-N-[3-(4-methyl-imidazol-1-yl)-5-trifluoromethyl-phenyl]-3-(4-pyridin-3-yl-pyrimidin-2-ylamino)-benzamide.

The third embodiment of the present invention is directed to the diphosphate salt of 4-methyl-N-[3-(4-methyl-imidazol-1-yl)-5-trifluoromethyl-phenyl]-3-(4-pyridin-3-yl-pyrimidin-2-ylamino)-benzamide. The $H_3PO_4$ di-salt can be produced from methanol when two equivalents phosphoric acid are used. The weight loss (room temperature to 200° C.) is about 0.2%, and the sample decomposes at about 210° C. The XRPD pattern for the diphosphate salt of 4-methyl-N-[3-(4-methyl-imidazol-1-yl)-5-trifluoromethyl-phenyl]-3-(4-pyridin-3-yl-pyrimidin-2-ylamino)-benzamide is shown in FIG. 3.

Figure 4:
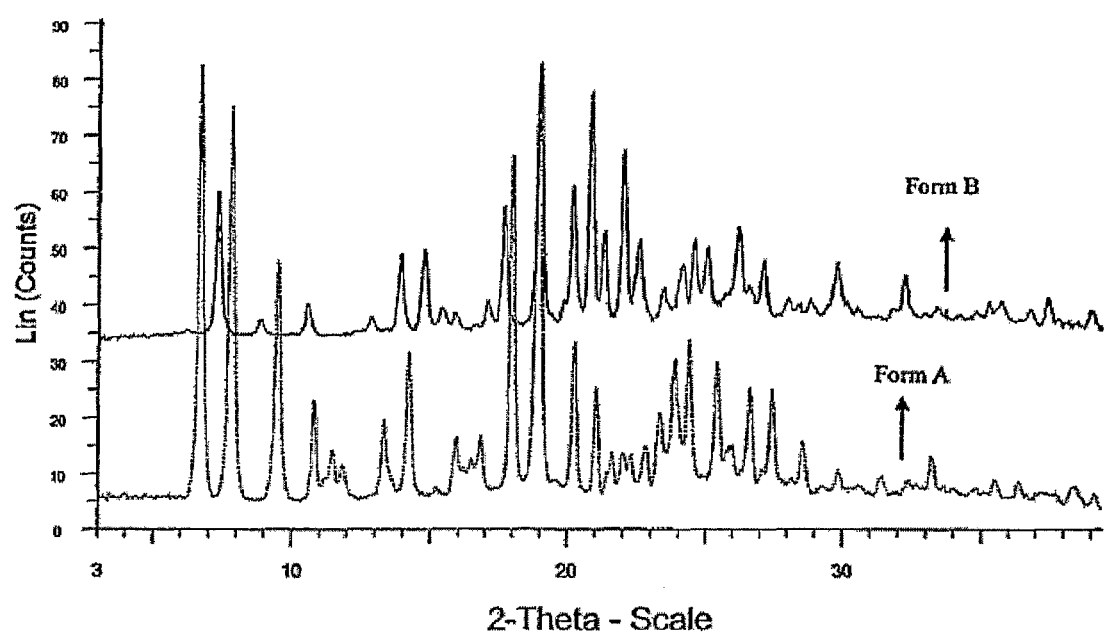
FIG. 4 shows the x-ray powder diffraction patterns for forms A and B of the sulfate salt of 4-methyl-N-[3-(4-methyl-imidazol-1-yl)-5-trifluoromethyl-phenyl]-3-(4-pyridin-3-yl-pyrimidin-2-ylamino)-benzamide.

The fourth embodiment of the present invention is directed to the sulfate salt of 4-methyl-N-[3-(4-methyl-imidazol-1-yl)-5-trifluoromethyl-phenyl]-3-(4-pyridin-3-yl-pyrimidin-2-ylamino)-benzamide. The $H_2SO_4$ salt (form B) is reproducibly produced from methanol when one equivalent sulfuric acid is used. The weight loss (room temperature to 200° C.) is about 0.15%, and the sample melts with decomposition at about 206° C. Its crystal structure ranges from poor to good. One other form (form A) and an amorphous form were isolated. The XRPD patterns for forms A and B of the sulfate salt of 4-methyl-N-[3-(4-methyl-imidazol-1-yl)-5-trifluoromethyl-phenyl]-3-(4-pyridin-3-yl-pyrimidin-2-ylamino)-benzamide are shown in FIG. 4.

Figure 5:
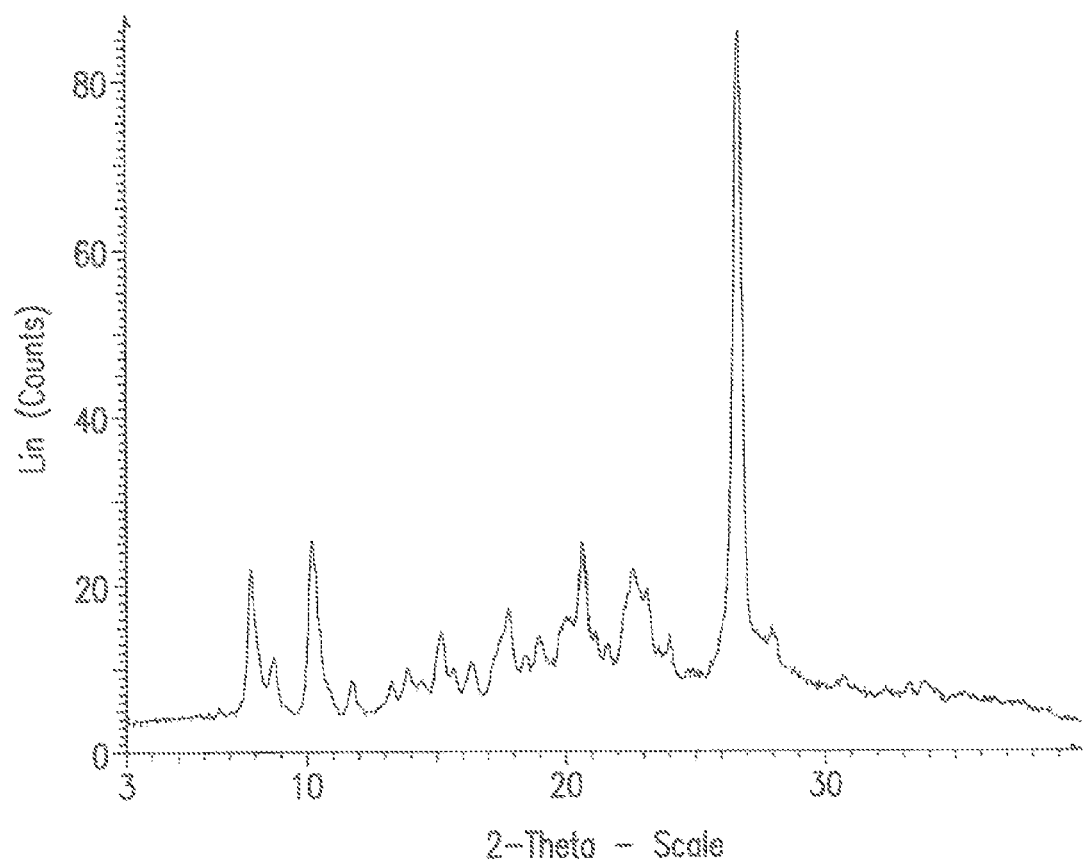
FIG. 5 shows the x-ray powder diffraction pattern for the methane sulfonate (mesylate) salt of 4-methyl-N-[3-(4-methyl-imidazol-1-yl)-5-trifluoromethyl-phenyl]-3-(4-pyridin-3-yl-pyrimidin-2-ylamino)-benzamide.

The fifth embodiment of the present invention is directed to the methane sulfonate (mesylate) salt of 4-methyl-N-[3-(4-methyl-imidazol-1-yl)-5-trifluoromethyl-phenyl]-3-(4-pyridin-3-yl-pyrimidin-2-ylamino)-benzamide. This salt is reproducibly produced from ethyl acetate when one equivalent methane sulfonic acid is used. The weight loss (room temperature to 150° C.) is about 0.44%, and the sample melts at about 160° C. and decomposes at about 260° C. Its crystal structure is poor. The XRPD pattern for the methane sulfonate salt of 4-methyl-N-[3-(4-methyl-imidazol-1-yl)-5-trifluoromethyl-phenyl]-3-(4-pyridin-3-yl-pyrimidin-2-ylamino)-benzamide is shown in FIG. 5.

Figure 6:
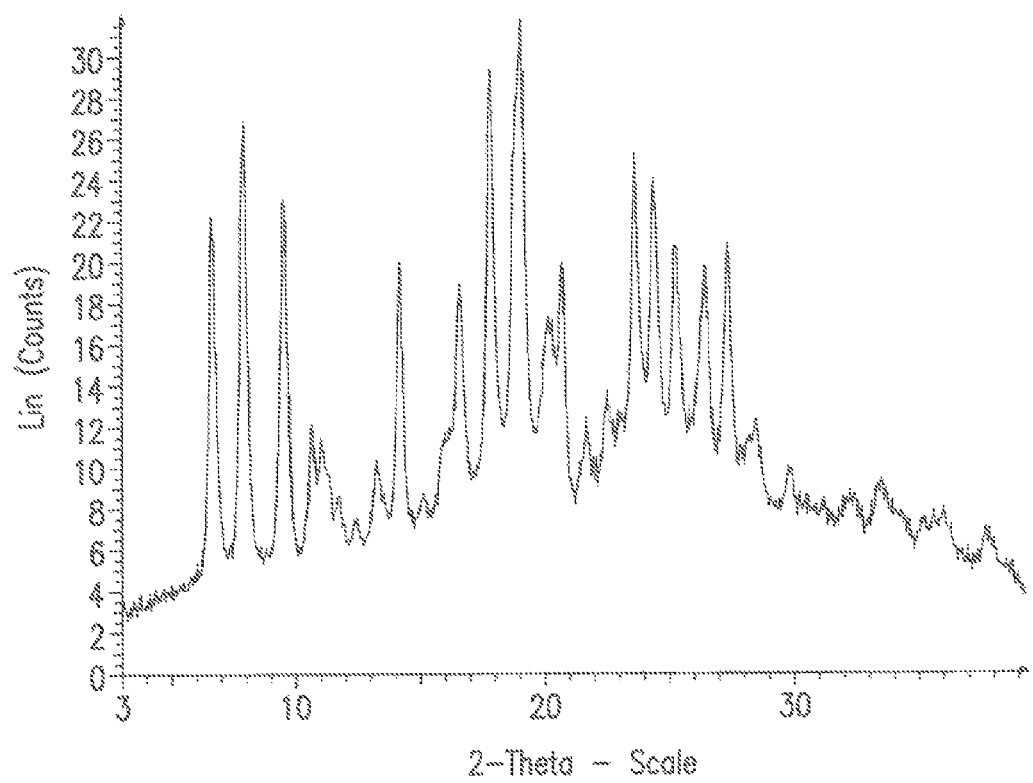
FIG. 6 shows the x-ray powder diffraction pattern for the ethane sulfonate salt of 4-methyl-N-[3-(4-methyl-imidazol-1-yl)-5-trifluoromethyl-phenyl]-3-(4-pyridin-3-yl-pyrimidin-2-ylamino)-benzamide.

The sixth embodiment of the present invention is directed to the ethane sulfonate salt of 4-methyl-N-[3-(4-methyl-imidazol-1-yl)-5-trifluoromethyl-phenyl]-3-(4-pyridin-3-yl-pyrimidin-2-ylamino)-benzamide. This salt is reproducibly produced from ethyl acetate when one equivalent ethane sulfonic acid is used. The weight loss (room temperature to 150° C.) is about 0.74%, and the sample melts at about 259° C. and decomposes at about 220° C. Its crystal structure is poor. The XRPD pattern for the ethane sulfonate salt of 4-methyl-N-[3-(4-methyl-imidazol-1-yl)-5-trifluoromethyl-phenyl]-3-(4-pyridin-3-yl-pyrimidin-2-ylamino)-benzamide is shown in FIG. 6.

Figure 7:
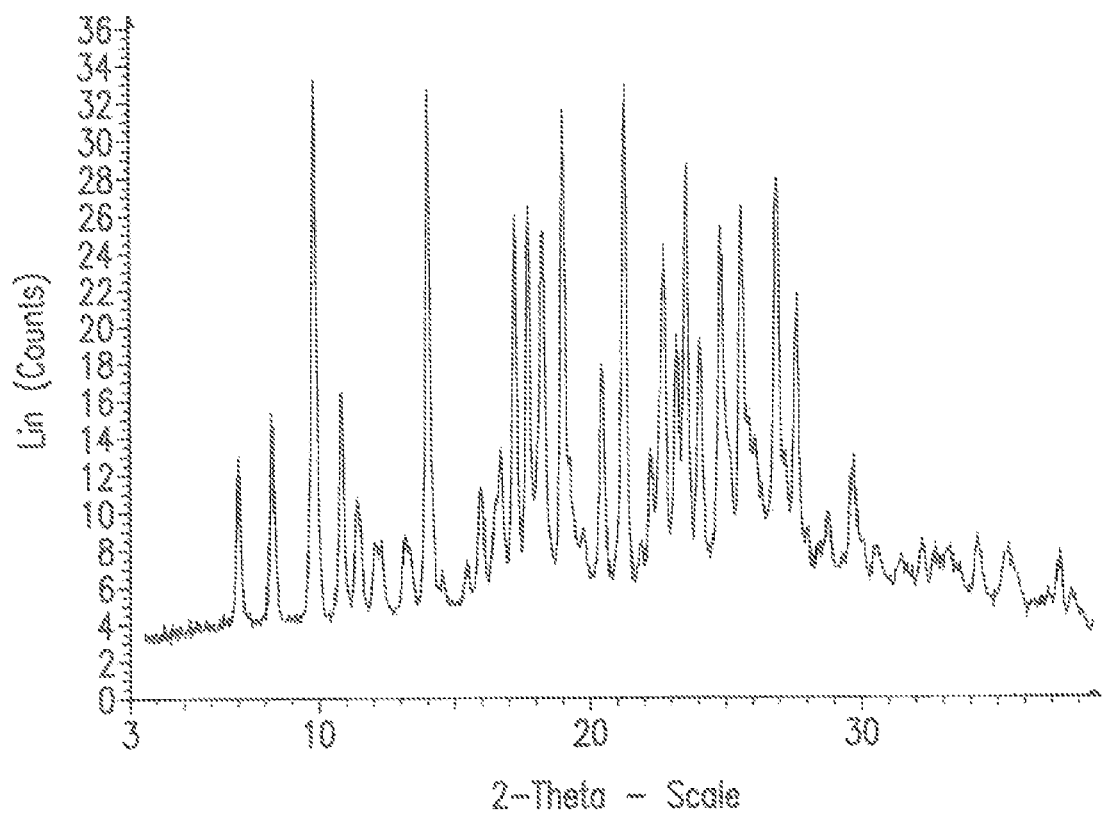
FIG. 7 shows the x-ray powder diffraction pattern for the benzene sulfonate salt of 4-methyl-N-[3-(4-methyl-imidazol-1-yl)-5-trifluoromethyl-phenyl]-3-(4-pyridin-3-yl-pyrimidin-2-ylamino)-benzamide.

The seventh embodiment of the present invention is directed to the benzene sulfonate salt of 4-methyl-N-[3-(4-methyl-imidazol-1-yl)-5-trifluoromethyl-phenyl]-3-(4-pyridin-3-yl-pyrimidin-2-ylamino)-benzamide. This salt is reproducibly produced from ethyl acetate when one equivalent benzene sulfonic acid is used. The weight loss (room temperature to 250° C.) is about 0.63%, and the sample melts with decomposition at about 260° C. Its crystal structure ranges from poor to good. The XRPD pattern for the benzene sulfonate salt of 4-methyl-N-[3-(4-methyl-imidazol-1-yl)-5-trifluoromethyl-phenyl]-3-(4-pyridin-3-yl-pyrimidin-2-ylamino)-benzamide is shown in FIG. 7.

Figure 8:
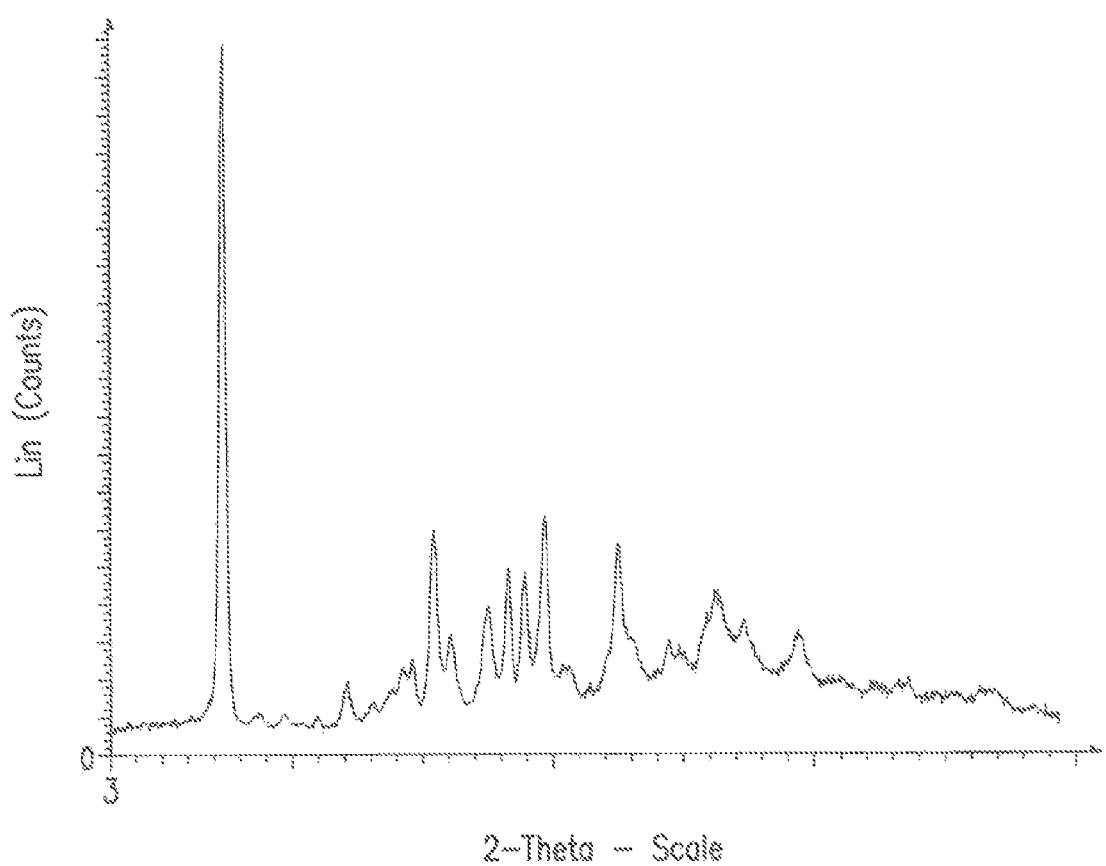
FIG. 8 shows the x-ray powder diffraction pattern for the p-toluene sulfonate salt of 4-methyl-N-[3-(4-methyl-imidazol-1-yl)-5-trifluoromethyl-phenyl]-3-(4-pyridin-3-yl-pyrimidin-2-ylamino)-benzamide.

The eighth embodiment of the present invention is directed to the p-toluene sulfonate salt of 4-methyl-N-[3-(4-methyl-imidazol-1-yl)-5-trifluoromethyl-phenyl]-3-(4-pyridin-3-yl-pyrimidin-2-ylamino)-benzamide. This salt is reproducibly produced from ethyl acetate when one equivalent p-toluene sulfonic acid is used. The weight loss (room temperature to 150° C.) is about 0.26%, and the sample melts at about 187° C. and decomposes at about 256° C. Its crystal structure ranges from good to excellent. The XRPD pattern for the p-toluene sulfonate salt of 4-methyl-N-[3-(4-methyl-imidazol-1-yl)-5-trifluoromethyl-phenyl]-3-(4-pyridin-3-yl-pyrimidin-2-ylamino)-benzamide is shown in FIG. 8.

Another embodiment of the present invention is directed to a method of preparing a variety of crystalline salts of 4-methyl-N-[3-(4-methyl-imidazol-1-yl)-5-trifluoromethyl-phenyl]-3-(4-pyridin-3-yl-pyrimidin-2-ylamino)-benzamide according to the following scheme:

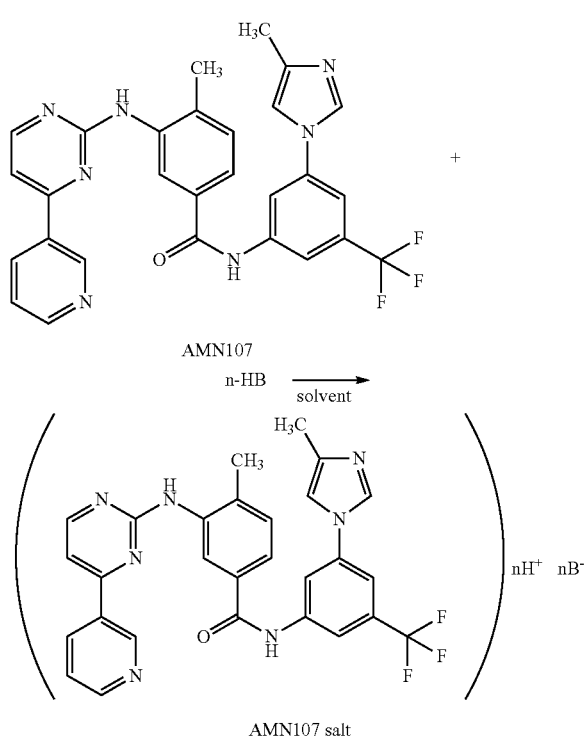

AMN107

AMN107 salt

More specifically, 4-methyl-N-[3-(4-methyl-imidazol-1-yl)-5-trifluoromethyl-phenyl]-3-(4-pyridin-3-yl-pyrimidin-2-ylamino)-benzamide salts are made by reacting 4-methyl-N-[3-(4-methyl-imidazol-1-yl)-5-trifluoromethyl-phenyl]-3-(4-pyridin-3-yl-pyrimidin-2-ylamino)-benzamide free base with an acid of formula HB in a solvent. Such reaction is typically conducted in two steps, though it is within the scope of this invention to simply combine both the free base and the acid in the solvent at the same time.

In a first step, 4-methyl-N-[3-(4-methyl-imidazol-1-yl)-5-trifluoromethyl-phenyl]-3-(4-pyridin-3-yl-pyrimidin-2-ylamino)-benzamide free base is dissolved or suspended in an appropriate amount of solvent at an appropriate temperature. Solvents suitable for use in the present invention include, without limitation, methanol, ethanol, 2-propanol, acetone, ethyl acetate, acetonitrile, tetrahydrofuran and combinations thereof. It is within the skill of one of ordinary skill in the art to determine suitable amounts of base to be used, as well as suitable reaction temperatures.

In a second step of the present inventive method, the 4-methyl-N-[3-(4-methyl-imidazol-1-yl)-5-trifluoromethyl-phenyl]-3-(4-pyridin-3-yl-pyrimidin-2-ylamino)-benzamide free base is treated with an appropriate acid of the formula HB. Given the pKa values for 4-methyl-N-[3-(4-methyl-imidazol-1-yl)-5-trifluoromethyl-phenyl]-3-(4-pyridin-3-yl-pyrimidin-2-ylamino)-benzamide free base of 5.1 and 3.9, salt forming acids with a pKa of ≦3.1 have the potential to form stable crystalline salts therewith. Suitable acids include, without limitation, inorganic acids such as hydrochloric acid, phosphoric acid, sulfuric acid, and sulfonic acid and organic acids such as methane sulfonic acid, ethane sulfonic acid, benzene sulfonic acid, p-toluene sulfonic acid, citric acid, fumaric acid, gentisic acid, malonic acid, maleic acid, and tartaric acid.

In optional steps of the present inventive method, the 4-methyl-N-[3-(4-methyl-imidazol-1-yl)-5-trifluoromethyl-phenyl]-3-(4-pyridin-3-yl-pyrimidin-2-ylamino)-benzamide salt is isolated by filtration or some other suitable means and the isolated salt is dried to remove residual solvent. In a preferred embodiment of this invention, the hydrochloride salt is first obtained as a methanol solvate which must be exposed to moisture in order to convert to the monohydrate hydrochloride salt.

A particularly preferred embodiment of the present invention is directed to a method of preparing 4-methyl-N-[3-(4-methyl-imidazol-1-yl)-5-trifluoromethyl-phenyl]-3-(4-pyridin-3-yl-pyrimidin-2-ylamino)-benzamide monohydrochloride monohydrate comprising the steps of:

(a) combining 4-methyl-N-[3-(4-methyl-imidazol-1-yl)-5-trifluoromethyl-phenyl]-3-(4-pyridin-3-yl-pyrimidin-2-ylamino)-benzamide free base and hydrochloric acid in methanol under a nitrogen atmosphere;
(b) heating the reaction mixture to a temperature ranging from about 42-50° C.;
(c) stirring the reaction mixture;
(d) filtering the reaction mixture while maintaining the temperature above 40° C. to obtain a clear solution;
(e) cooling the clear solution to about 30° C. while stirring under nitrogen atmosphere;
(f) seeding the solution;
(g) cooling the seeded solution to about 23° C.;
(h) stirring the solution to obtain a suspension;
(i) cooling the suspension to about −10° C.;
(j) stirring the suspension;
(k) filtering solids;
(l) rinsing solids with cold methanol; and
(m) drying the solids at about 50-55° C. and 10-20 torr to obtain 4-methyl-N-[3-(4-methyl-imidazol-1-yl)-5-trifluoromethyl-phenyl]-3-(4-pyridin-3-yl-pyrimidin-2-ylamino)-benzamide monohydrochloride monohydrate salt.

In more preferred embodiments, stirring is conducted for about 15 minutes in step (c), cooling is accomplished over a period of about 30 minutes in step (e), cooling is accomplished over a period of about 45 minutes in step (g), stirring is conducted for about 3 hours in step (h), cooling is accomplished over a period of about 1.5 hours in step (i), stirring is conducted for about 30 minutes in step (j), the cold methanol of step (l) has a temperature of about −10° C., and/or drying is accomplished over a period of about 8-16 hours.

The tenth embodiment of the present invention is directed to a pharmaceutical composition comprising:

(a) a therapeutically effective amount of a salt of 4-methyl-N-[3-(4-methyl-imidazol-1-yl)-5-trifluoromethyl-phenyl]-3-(4-pyridin-3-yl-pyrimidin-2-ylamino)-benzamide; and
(b) at least one pharmaceutically acceptable carrier, diluent, vehicle or excipient.

A "therapeutically effective amount" is intended to mean the amount of the inventive salt that, when administered to a subject in need thereof, is sufficient to effect treatment for disease conditions alleviated by the inhibition of protein kinase activity. The amount of a given compound of the invention that will be therapeutically effective will vary depending upon factors such as the disease condition and the severity thereof, the identity of the subject in need thereof, etc., which amount may be routinely determined by artisans of ordinary skill in the art.

The at least one pharmaceutically acceptable carrier, diluent, vehicle or excipient can readily be selected by one of ordinary skill in the art and will be determined by the desired mode of administration. Illustrative examples of suitable modes of administration include oral, nasal, parenteral, topical, transdermal, and rectal. The pharmaceutical compositions of this invention may take any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols.

The eleventh embodiment of the present invention is directed to a method of treating a disease which responds to an inhibition of protein kinase activity comprising the step of administering to a subject in need of such treatment a therapeutically effective amount of a salt of 4-methyl-N-[3-(4-methyl-imidazol-1-yl)-5-trifluoromethyl-phenyl]-3-(4-pyridin-3-yl-pyrimidin-2-ylamino)-benzamide. As noted above, illustrative modes of administration include oral, nasal, parenteral, topical, transdermal, and rectal. Administration of the crystalline form may be accomplished by administration of a pharmaceutical composition of the ninth embodiment of the invention or via any other effective means.

Specific embodiments of the invention will now be demonstrated by reference to the following examples. It should be understood that these examples are disclosed solely by way of illustrating the invention and should not be taken in any way to limit the scope of the present invention.

Example 1

Preparation of Monohydrochloride Monohydrate Salt ing solution was filtered through a polypropylene pad, while maintaining the batch temperature above 40° C. The clear solution was transferred under nitrogen atmosphere to another 1 L, 4-neck, and round-bottom flask equipped with a mechanical stirrer, a thermometer, and heating/cooling capacity. The batch was stirred and cooled to 30° C. over a period of 30 minutes. Seeds (20 mg) were added at this temperature, and the batch was cooled to 23° C. over a period of 45 minutes. The batch was stirred for an additional 3 hours to obtain a thick white suspension. The suspension was cooled to −10° C. over a period of 1.5 hours and stirred for an additional 30 minutes. Any solid was collected by filtration and rinsed with cold (−10° C.) methanol (20 mL). The solid was dried at 50-55° C./10-20 torr for 8-16 hours to obtain 4-methyl-N-[3-(4-methyl-imidazol-1-yl)-5-trifluoromethyl-phenyl]-3-(4-pyridin-3-yl-pyrimidin-2-ylamino)-benzamide monohydrochloride monohydrate salt (9.8 g) as a white solid.

$^1$H NMR 300 MHz, DMSO-$d_6$), δ 10.9 (s, 1H), 9.58 (s, 1H), 9.29 (s, 1H), 9.20 (s, 1H), 8.70 (d, 1H), 8.63 (s, 1H), 8.55 (d, 1H), 8.49 (d, 1H), 8.32 (d, 2H), 8.00 (s, 1H), 7.91 (s, 1H), 7.84 (d, 1H), 7.56-7.44 (m, 3H), 2.50 (s, 3H), 2.35 (s, 3H); x-ray diffraction pattern showing maxima at 2θ=7.4°, 9.4°, 11.6°, 12.1°, 15.8°, 19.3°, 19.6°, 22.1°, 24.1°, 25.7°.

Example 2

Preparation of Monophosphate Salt

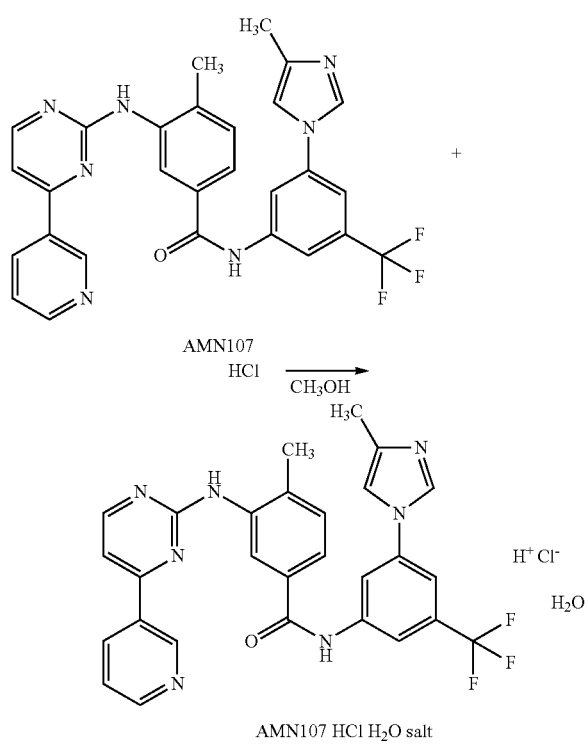
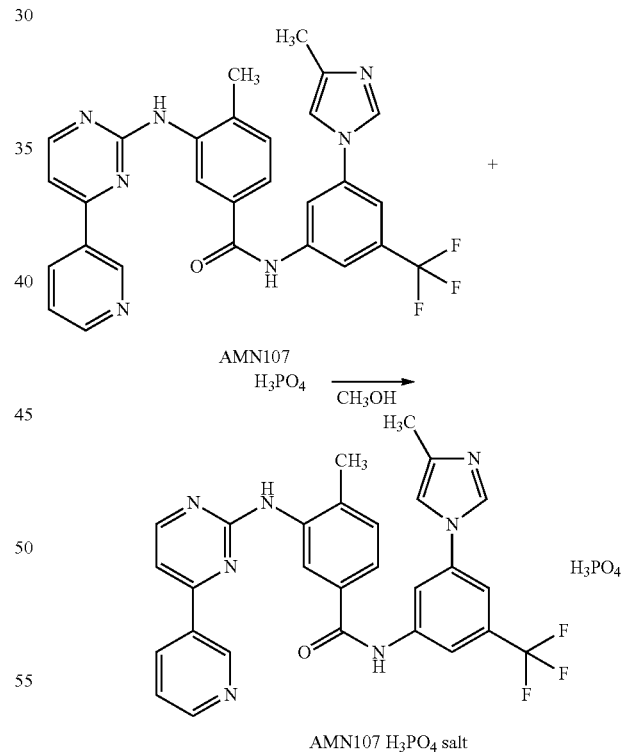

A 1 L, 4-neck, round-bottom flask equipped with a mechanical stirrer, a thermometer, heating/cooling capacity, and an addition funnel was charged in sequence with 4-methyl-N-[3-(4-methyl-imidazol-1-yl)-5-trifluoromethyl-phenyl]-3-(4-pyridin-3-yl-pyrimidin-2-ylamino)-benzamide free base (10 g), methanol (250 mL), and 37% hydrochloric acid (1.85 g) under nitrogen purge. The mixture was heated to 42-50° C. and stirred for an additional 15 minutes. The result- To a 1 L round-bottom flask equipped with a mechanical stirrer, a thermometer, and a condenser, 4 g of 4-methyl-N-[3-(4-methyl-imidazol-1-yl)-5-trifluoromethyl-phenyl]-3-(4-pyridin-3-yl-pyrimidin-2-ylamino)-benzamide free base and 500 mL of methanol were charged. The slurry was stirred and heated to 64° C. and held at that temperature for ~30 minutes. To the resulting clear solution, 7.5 mL of 1 M phosphorous acid solution (in methanol) was added. The mixture was stirred at 64° C. for one hour, cooled down to room temperature by natural cooling (cooling rate ~0.5° C./min) and held at room temperature for 3-4 hours. The solid was collected by filtration and was dried at 50-55° C./10-20 ton for 8-16 hours to obtain 4-methyl-N-[3-(4-methyl-imidazol-1-yl)-5-trifluoromethyl-phenyl]-3-(4-pyridin-3-yl-pyrimidin-2-ylamino)-benzamide monophosphate salt (3.25 g) as a white solid. Melting point=~208° C. (dec.); x-ray diffraction pattern showing maxima at 2θ=6.1°, 7.5°, 9.1°, 15.8°, 17.5°, 18.3°, 21.8°, 23.1°, 24.9°, 26.6°.

Example 3

Preparation of Methane Sulfonate Salt

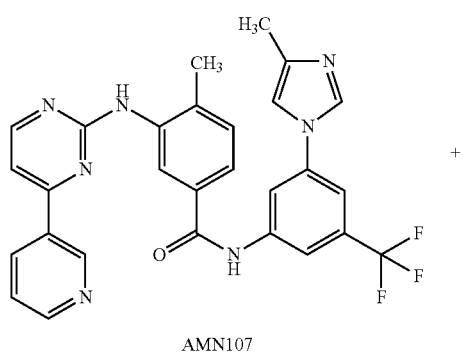

AMN107

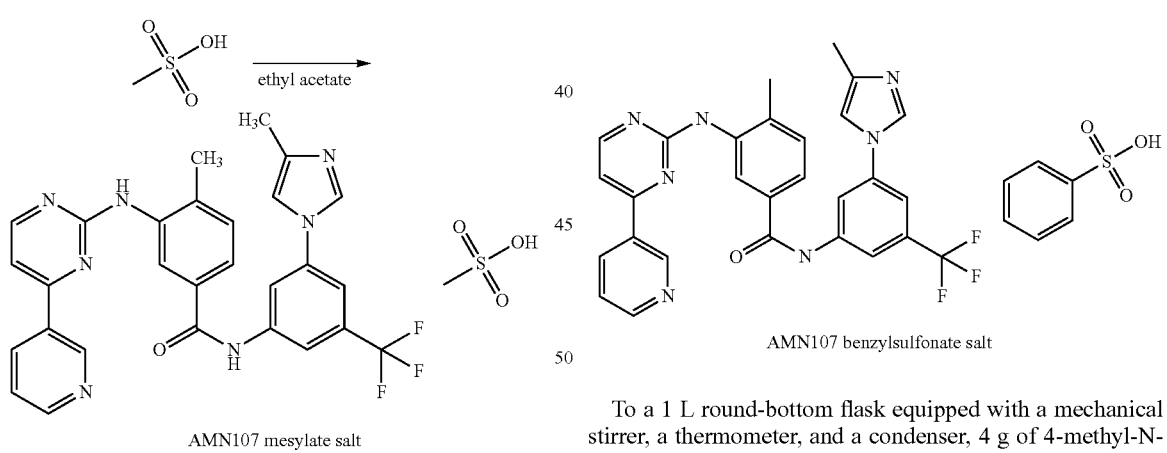

AMN107 mesylate salt

To a 75 mL reactor equipped with a temperature probe and a condenser, 307 mg of 4-methyl-N-[3-(4-methyl-imidazol-1-yl)-5-trifluoromethyl-phenyl]-3-(4-pyridin-3-yl-pyrimidin-2-ylamino)-benzamide free base and 30 mL of ethyl acetate were charged. The slurry was stirred and heated to 76° C. To the solution, 580 μL it of 1 M methane sulfonic acid solution (in ethyl acetate) was added. The mixture was stirred at 76° C. for six hours, cooled to 25° C. at a rate of 0.5° C./minute and held at 25° C. overnight. The solid was collected by filtration and was dried at 50-55° C./10-20 torr for 8-16 hours to obtain 4-methyl-N-[3-(4-methyl-imidazol-1-yl)-5-trifluoromethyl-phenyl]-3-(4-pyridin-3-yl-pyrimidin-2-ylamino)-benzamide mesylate salt (~250 mg) as a yellowish solid. X-ray diffraction pattern showing maxima at 2θ=7.7°, 10.1°, 20.3°, 26.2°.

Example 4

Preparation of Benzylsulfonate Salt

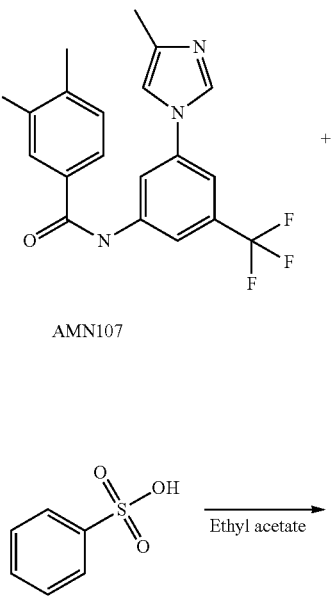

AMN107 benzylsulfonate salt

To a 1 L round-bottom flask equipped with a mechanical stirrer, a thermometer, and a condenser, 4 g of 4-methyl-N-[3-(4-methyl-imidazol-1-yl)-5-trifluoromethyl-phenyl]-3-(4-pyridin-3-yl-pyrimidin-2-ylamino)-benzamide free base and 500 mL of ethyl acetate were charged. The slurry was stirred and heated to 76° C. (reflux) and held at that temperature for 40 minutes. To the resulting clear solution, 7.5 mL of 1 M benzene sulfonic acid solution (in ethyl acetate) was added. The mixture was stirred at 76° C. for 5 hours, cooled down to room temperature by natural cooling (cooling rate ~0.5° C./min) and held at room temperature for ~1 hour. The solid was collected by filtration and was dried at 50-55° C./10-20 torr for 8-16 hours to obtain 4-methyl-N-[3-(4-methyl-imidazol-1-yl)-5-trifluoromethyl-phenyl]-3-(4-pyridin-3-yl-pyrimidin-2-ylamino)-benzamide mono benzyl sulfonate salt as a yellowish solid. Melting point=~260° C.;

x-ray diffraction pattern showing maxima at 2θ=6.5°, 7.8°, 9.4°, 10.4°, 13.7°, 17.0°, 17.5°, 17.9°, 18.8°, 21.2°.

Example 5

Preparation of p-Toluene Sulfonate Salt

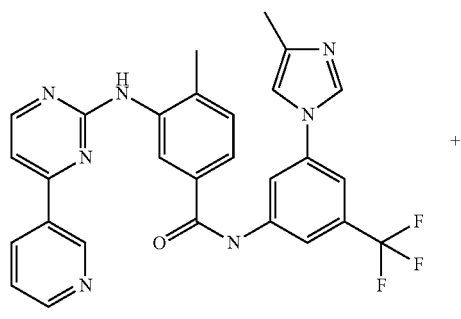
AMN107

+

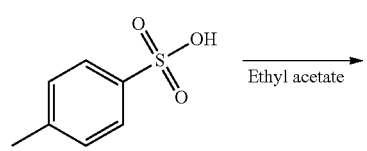
Ethyl acetate

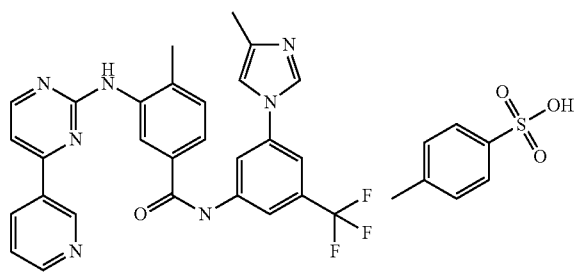
AMN107 p-tolysulfonate salt

To a 75 mL reactor equipped with a temperature probe and a condenser, 305.6 mg of 4-methyl-N-[3-(4-methyl-imidazol-1-yl)-5-trifluoromethyl-phenyl]-3-(4-pyridin-3-yl-pyrimidin-2-ylamino)-benzamide free base and 30 mL of ethyl acetate were charged. The slurry was stirred and heated to 76° C. To the solution, 580 µL of 1 M p-toluene sulfonic acid solution (in ethyl acetate) was added. The mixture was stirred at 76° C. for six hours, cooled to 25° C. at a rate of 0.5° C./minute and held at 25° C. overnight. The solid was collected by filtration and was dried at 50-55° C./10-20 torr for 8-16 hours to obtain 4-methyl-N-[3-(4-methyl-imidazol-1-yl)-5-trifluoromethyl-phenyl]-3-(4-pyridin-3-yl-pyrimidin-2-ylamino)-benzamide p-toluene sulfonate salt (~250 mg) as a white solid. Melting point=~187° C.; x-ray diffraction pattern showing maxima at 2θ=7.3°, 15.4°, 16.1°, 17.5°, 18.3°, 19.0°, 19.7°, 22.5°.

Example 6

Hydrochloride Salt 4-methyl-N-[3-(4-methyl-imidazol-1-yl)-5-trifluoromethyl-phenyl]-3-(4-pyridin-3-yl-pyrimidin-2-ylamino)-benzamide free base and about 400 mL methanol are charged into a flask. While stirring, 744.4 mg of 37% HCl solution is added dropwise. The slurry becomes clear. The solution is stirred for 30 minutes. The solution is concentrated to 100 mL. The solution is then stirred for 2 hours; a slurry is obtained. The slurry is filtered and dried under house vacuum overnight at 50° C. Polymorphic form B is obtained with a yield of about 72.6%.

Example 7

About 50-60 mg of form A of 4-methyl-N-[3-(4-methyl-imidazol-1-yl)-5-trifluoromethyl-phenyl]-3-(4-pyridin-3-yl-pyrimidin-2-ylamino)-benzamide free base was suspended in 0.75 mL of a listed solvent. The stoichiometric amount of a noted acid was subsequently added to the suspension. For inorganic acids, the mixture was stirred at ambient temperature for about 5 hours, and for sulfonic acids, it was stirred at 50° C. overnight. Solids were collected by filtration and analyzed by XRPD and NMR.

TABLE 1

Formation of Hydrochloride Salt

| | | Results | |
|---|---|---|---|
| Solvent | Comments | Crystallinity* | ¹H-NMR |
| Methanol | Slurry becomes thinner after HCl addition. | Good; form B | No solvent peak |
| Ethanol | Slurry becomes thinner after HCl addition. | Good; forms A & B | No solvent peak |
| 2-Propanol | Slurry becomes thinner after HCl addition. | Good; form A | No solvent peak |
| Acetone | Slurry becomes thinner after HCl addition. | Excellent; form A | — |
| Ethyl acetate | Slurry becomes thinner after HCl addition. | Good; forms A & B | — |
| Tetrahydrofuran | Slurry becomes thinner after HCl addition. | Excellent; form A | — |
| Acetonitrile | Slurry becomes thinner after HCl addition. | Excellent; forms A & B | — |

*excellent = when main peaks are sharp and their intensities above 70 counts good = when main peaks are sharp and their intensities within 30-70 counts

TABLE 2

Formation of Sulfate Salt

| Solvent | Comments | Results Crystallinity* | $^1$H-NMR |
|---|---|---|---|
| Methanol | Slurry becomes thinner after $H_2SO_4$ addition. | Good; forms A & B | No solvent peak |
| Ethanol | Slurry becomes thinner after $H_2SO_4$ addition. | Good; form B | No solvent peak |
| 2-Propanol | Slurry becomes thinner after $H_2SO_4$ addition. | Poor | — |
| Acetone | Slurry becomes thinner after $H_2SO_4$ addition. | Poor | — |
| Ethyl acetate | Slurry becomes thinner after $H_2SO_4$ addition. | Poor | — |
| Tetrahydrofuran | Slurry becomes thinner after $H_2SO_4$ addition. | Poor | — |
| Acetonitrile | Slurry becomes thinner after $H_2SO_4$ addition. | Poor | — |

*good = when main peaks are sharp and their intensities within 30-70 counts poor = when main peaks are broad and their intensities below 30 counts; could be amorphous salt and free base form A

TABLE 3

Formation of Methane Sulfonate Salt

| Solvent | Comments | Results Crystallinity* | $^1$H-NMR |
|---|---|---|---|
| Acetone | Slurry became thinner and turned yellow after acid addition. It did not become clear at 50° C. | Poor | 1) 1.3% (w) acetone<br>2) acid:base = 1.2:1.0 |
| Tetrahydrofuran | Slurry became thinner and turned yellow after acid addition. It did not become clear at 50° C. | Amorphous | — |

*poor = when main peaks are broad and their intensities below 30 counts

TABLE 4

Formation of Ethane Sulfonate Salt

| Solvent | Comments | Results Crystallinity* | $^1$H-NMR |
|---|---|---|---|
| Acetone | Slurry became thinner and turned yellow after acid addition. It did not become clear at 50° C. | Good | 1) 0.9% (w) acetone<br>2) acid:base = 1.4:1.0 |
| Tetrahydrofuran | Slurry became thinner and turned yellow after acid addition. It did not become clear at 50° C. | Poor | — |

*good = when main peaks are sharp and their intensities within 30-70 counts poor = when main peaks are broad and their intensities below 30 counts The ethane sulfonate salt from acetone has an x-ray diffraction pattern showing maxima at 2θ=6.6°, 7.9°, 9.5°, 14.2°, 17.8°.

TABLE 5

Formation of Benzene Sulfonate Salt

| Solvent | Comments | Results Crystallinity* | $^1$H-NMR |
|---|---|---|---|
| Tetrahydrofuran | Slurry became thinner and turned yellow after acid addition. It did not become clear at 50° C. | Poor | 1) 1.2% (w) THF<br>2) acid:base = 1.4:1.0 |
| Acetone | Slurry became thinner and turned yellow after acid addition. It did not become clear at 50° C. | Poor | — |

*poor = when main peaks are broad and their intensities below 30 counts

TABLE 6

Formation of p-Toluene Sulfonate Salt

| Solvent | Comments | Results Crystallinity* | $^1$H-NMR |
|---|---|---|---|
| Tetrahydrofuran | Slurry became thinner after acid addition. It did not become clear at 50° C. White solid was obtained by filtration. | Good | 1) 4.6% (w) THF<br>2) acid:base = 1.2:1.0 |
| Acetone | Slurry became thinner after acid addition. It did not become clear at 50° C. White solid was obtained by filtration. | Good | — |

*good = when main peaks are sharp and their intensities within 30-70 counts

Example 8

About 300-310 mg of form B of 4-methyl-N-[3-(4-methyl-imidazol-1-yl)-5-trifluoromethyl-phenyl]-3-(4-pyridin-3-yl-pyrimidin-2-ylamino)-benzamide free base was suspended in 9 mL of 2-propanol for HCl and 15 mL, acetone for the sulfonic acids. The stoichiometric amount of the noted acid was subsequently added to the suspension. For HCl, the mixture was stirred at ambient temperature for 5 hours, and for sulfonic acids, it was stirred at 50° C. overnight. Then, the mixture was cooled to ambient temperature, collected by filtration and analyzed by XRPD and NMR.

TABLE 7

| Acid | Comments | Results Crystallinity | $^1$H-NMR |
|---|---|---|---|
| HCl | After HCl addition, the slurry became yellow, then off-white. After 4 hours of holding, the slurry was like paste, difficult to pour and filter. | 1) good<br>2) form A | 1) shifts changed<br>2) no solvent peak |
| Methane sulfonic acid | Slurry became thinner and turned yellow after acid addition. It did not become clear at 50° C. | Poor | 1) shifts changed<br>2) 0.67% (w) acetone |
| Ethane sulfonic acid | Slurry became thinner and turned yellow after acid addition. It did not become clear at 50° C. | Poor | 1) shifts changed<br>2) no solvent peak |
| p-Toluene sulfonic acid | Slurry became thinner and turned yellow after acid addition. It did not become clear at 50° C. White solid was obtained by filtration. | Good | 1) shifts changed<br>2) no solvent peak |

Example 9

About 100 mg of form B of 4-methyl-N-[3-(4-methyl-imidazol-1-yl)-5-trifluoromethyl-phenyl]-3-(4-pyridin-3-yl-pyrimidin-2-ylamino)-benzamide free base was suspended in 15 mL of methanol for the inorganic acids and in 15 mL THF for the sulfonic acids noted below. The stoichiometric amount of the listed acid was subsequently added to the suspension, except for $H_3PO_4$, for which two equivalents were added. The solution was stirred at 50° C. for about 5 hours and then cooled to ambient temperature. Solids were collected by filtration if slurry formed; otherwise, a slow $N_2$ flow was applied to evaporate some solvent to yield thicker slurry for filtration. The solids were analyzed by XRPD and NMR.

TABLE 8

| Acid | Comments | Results Crystallinity | $^1$H-NMR |
|---|---|---|---|
| HCl | The slurry became clear while heating and remained so. Slow $N_2$ | 1) good<br>2) Form B | 1) shifts changed<br>2) no solvent peak |

TABLE 8-continued

| Acid | Comments | Results Crystallinity | $^1$H-NMR |
|---|---|---|---|
| | flow was used to evaporate some solvent. | | |
| $H_2SO_4$ | The slurry became clear after heating. It became slurry during cooling. | 1) good 2) form A + B | 1) shifts changed 2) <2% methanol |
| $H_3PO_4$ (diphosphate) | Slurry becomes thicker after acid addition. | 1) excellent 2) different from free base and mono-salt | 1) no shift change 2) no solvent peak |
| Methane sulfonic acid | Slurry became thinner and turned yellow after acid addition. It did not become clear at 50° C. | Poor | 1) shifts changed 2) no solvent peak |
| Benzene sulfonic acid | Slurry became thinner and turned yellow after acid addition. It did not become clear at 50° C. | Good | 1) shifts changed 2) no solvent peak |
| p-Toluene sulfonic acid | Slurry became thinner and turned yellow after acid addition. It did not become clear at 50° C. White solid was obtained by filtration. | Excellent | 1) shifts changed 2) no solvent peak |

Elemental analysis was used to check salt formation for the diphosphate salt. The results are as follows:

TABLE 9

| | C | H | N | P |
|---|---|---|---|---|
| Theoretical | 45.91 | 3.83 | 13.39 | 8.47 |
| $H_3PO_4$ above | 45.86 | 3.81 | 13.32 | 9.01 |

Example 10

About 100 mg of form B of 4-methyl-N-[3-(4-methyl-imidazol-1-yl)-5-trifluoromethyl-phenyl]-3-(4-pyridin-3-yl-pyrimidin-2-ylamino)-benzamide free base was suspended in 15 mL of methanol for HCl and $H_2SO_4$ and in 15 mL of ethyl acetate for methane sulfonic acid. The listed amount of the listed acid was subsequently added to the suspension. The solution was stirred at ambient temperature (HCl) or 50° C. ($H_2SO_4$ and methane sulfonic acid). The solids were obtained by evaporating solvent to dryness using a slow $N_2$ flow and analyzed by XRPD and NMR.

Example 11

About 300 mg of form B of 4-methyl-N-[3-(4-methyl-imidazol-1-yl)-5-trifluoromethyl-phenyl]-3-(4-pyridin-3-yl-pyrimidin-2-ylamino)-benzamide free base was suspended in 30 mL of methanol for the inorganic acids and in 30 mL ethyl acetate for the sulfonic acids. The suspension was heated to reflux temperature –64° C. for methanol and 76° C. for ethyl acetate. The stoichiometric amount of the listed acid, dissolved in the corresponding solvent, was subsequently added to the solution. The solution was stirred under reflux for 5 hours and then cooled to ambient temperature. The solid was collected by filtration and analyzed by XRPD.

TABLE 11

| Acid | Comments | Form |
|---|---|---|
| $H_2SO_4$ | The slurry became clear under reflux. Solid precipitated out after holding. | 1) sulfate 2) form B |
| $H_3PO_4$ | The slurry became clear under reflux. Solid precipitated out after holding. | Monophosphate |

TABLE 10

| Acid | Comments | Results Crystallinity | $^1$H-NMR |
|---|---|---|---|
| 1 equivalent HCl | The slurry became clear while heating and remained so. | 1) good 2) form B | 1) shifts changed 2) no solvent peak |
| 2 equivalents HCl | The slurry became clear while heating and remained so. | Amorphous | — |
| 0.5 equivalents $H_2SO_4$ | The slurry became clear while heating and remained so. | 1) good 2) form A & free base form B | 1) shifts changed 2) small solvent peak |
| 1 equivalent $H_2SO_4$ | The slurry became clear after acid addition and remained so. | 1) good 2) form A | 1) shifts changed 2) no solvent peak |
| 1 equivalent methane sulfonic acid | Slurry became clear after acid addition and remained so after 4 hours holding. | Poor | 1) acid:base = 1.3:1.0 2) no solvent peak |
| 2 equivalents methane sulfonic acid | Slurry became clear after acid addition and remained so after 4 hours holding. | Poor | 1) acid:base = 1.9:1.0 2) no solvent peak |

TABLE 11-continued

| Acid | Comments | Form |
|---|---|---|
| Methane sulfonic acid | The solution remained slurry under reflux. It became thinner and turned yellow after acid addition. | Methane sulfonate |
| Benzene sulfonic acid | The solution remained slurry under reflux. It became thinner and turned yellow after acid addition. | Benzene sulfonate |
| p-Toluene sulfonic acid | The solution remained slurry under reflux. It became clear after acid addition. | p-Toluene sulfonate |

Thermal Behavior

The LOD and decomposition temperature of the salts of the invention were determined by TGA, and the melting point was determined by DSC.

TABLE 12

| Salt | LOD | Decomposition temperature (° C.)* | Melting point (° C.) |
|---|---|---|---|
| Hydrochloride (form B) | 2.60% (RT-150° C.) 4.87% (150-250° C.) | | |
| Monophosphate | 0.29% (RT-200° C.) | 212 | ~208 |
| Sulfate (form B) | 0.15% (RT-200° C.) | 201 | 1) 126.5 2) 206.2 |
| Methane sulfonate | 0.44% (RT-150° C.) | 260 | 160.1 |
| Ethane sulfonate | 0.74% (RT-150° C.) | 220 | 1) 259.2 2) 261.3 |
| Benzene sulfonate | 0.63% (RT-250° C.) | 260 | >258.7 |
| p-Toluene sulfonate | 0.26% (RT-150° C.) | 256 | 1) 187 2) 232 |

*The decomposition temperature was determined by the onset of the first derivative of the sample weight loss v. temperature of TGA data Hygroscopicity The hygroscopicity of the salts of the invention was determined by TGA after one day at ambient temperature and 93% relative humidity.

TABLE 13

| Salt | % moisture gain |
|---|---|
| Hydrochloride (form B) | 0.20 |
| Monophosphate | 1.33 |
| Sulfate (form B) | 0.22 |
| Methane sulfonate | 0.22 |
| Ethane sulfonate | 1.11 |
| Benzene sulfonate | 0.11 |
| p-Toluene sulfonate | 1.02 |
| Control - free base form B | 0.08 |

It should be noted that, upon further testing, hygroscopicity results have varied. At least with regard to the hydrochloride salt, moisture is lost too quickly upon testing to capture the true value; such may be true for the other salts as well.

Solubility

The solubility of the salts of the invention was determined in pH 6.8, pH 3.0 and pH 1.0 buffers by suspending 1-5 mg of each salt in 10 mL of corresponding aqueous solution. The samples were allowed to equilibrate at ambient temperature for at least 20 hours for pH 6.8 and 3.0 or about 5 hours for pH 1.0. The supernatant was filtered and used for the solubility determination by UV-VIS spectroscopy. The solid residue was analyzed by XRPD.

TABLE 14

| Solute | Solubility at pH 6.8 (μg/mL) | Solubility at pH 3.0 (μg/mL) | Solubility at pH 1.0 (μg/mL) |
|---|---|---|---|
| Hydrochloride salt (form B) | 0.3 | 0.9 | 1040 |
| Monophosphate salt | — | — | 1160 |
| Sulfate salt (form B) | 0.1 | 6.5 | 1380 |
| Methane sulfonate salt | 0.4 | 5.2 | 1330 |
| Ethane sulfonate salt | 0.4 | 2.8 | — |
| Benzene sulfonate salt | <3.0 | — | 1420 |
| p-Toluene sulfonate salt | <8.0 | <10.0 | 1340 |
| Control - free base form B | 0.2 | 2.8 | 839 |

Comparative Testing

The stability of both 4-methyl-N-[3-(4-methyl-imidazol-1-yl)-5-trifluoromethyl-phenyl]-3-(4-pyridin-3-yl-pyrimidin-2-ylamino)-benzamide free base (form B) and 4-methyl-N-[3-(4-methyl-imidazol-1-yl)-5-trifluoromethyl-phenyl]-3-(4-pyridin-3-yl-pyrimidin-2-ylamino)-benzamide monohydrate hydrochloride salt (foam B) were evaluated as described below.

TABLE 15

| | Salt form | | | |
|---|---|---|---|---|
| | Free base (form B) | | Hydrochloride monohydrate (form B) | |
| Test conditions | Degradation products Assay [% area] | Appearance | Degradation products Assay [% area] | Appearance |
| Unstressed | 0.00 100.99 [100.00] | — | 0.00 99.10 [100.00] | — |
| 0.1% solutions or suspensions, 1 week at 80° C. | | | | |
| pH 1 (pH measured: 1.26) | 60.61 | A* | 62.06 | A* |
| PH 1; 1 week @ 50° C. | 50.22 [45.31] 6.58 94.01 [93.44] | A* | 46.68 [42.93] 6.86 94.14 [93.21] | A* |
| pH 2 (pH measured: 2.00) | 5.20 96.00 [94.86] | B↓ | 8.41 91.77 [91.61] | B↓ |
| pH 3 (pH measured: 2.94) | 0.00 102.19 [100.00] | A↓ | 0.00 98.84 [100.00] | B↓ |
| pH 5 (pH measured: 5.01) | 0.00 100.80 [100.00] | A↓ | 0.00 100.02 [100.00] | A↓ |

TABLE 15-continued

| Test conditions | Salt form | | | |
|---|---|---|---|---|
| | Free base (form B) | | Hydrochloride monohydrate (form B) | |
| | Degradation products Assay [% area] | Appearance | Degradation products Assay [% area] | Appearance |
| pH 7 (pH measured: 6.02) | 0.00<br>100.14 [100.00] | A↓ | 0.00<br>99.56 [100.00] | B↓ |
| pH 9 (pH measured: 8.92) | 0.00<br>99.19 [100.00] | A↓ | 0.00<br>101.19 [100.00] | B↓ |
| pH 11 (pH measured: 10.86) | 0.00<br>100.50 [100.00] | A↓ | 0.00<br>102.19 [100.00] | B↓ |
| Water (pH measured: 4.74) (pH measured for HCl salt: 4.22) | 0.00<br>101.93 [100.00] | A↓ | 0.00<br>101.43 [100.00] | A↓ |
| Ethanol | 0.04<br>99.85 [99.96] | A* | 0.06<br>100.41 [100.00] | A* |
| Acetonitrile | 0.00<br>100.16 [100.00] | A* | 0.00<br>100.33 [100.00] | B↓ |
| Methanol | 1.06<br>98.04 [98.90] | A* | 1.29<br>99.169 [98.72] | A* |
| 2% solutions or suspensions, 1 day at room temperature | | | | |
| 0.5% CMC | 0.00<br>98.28 [100.00] | A↓ | 0.00<br>103.06 [100.00] | A↓ |
| 0.5% HPMC cellulose 4000 | 0.00<br>98.27 [100.00] | A↓ | 0.00<br>100.44 [100.00] | A↓ |
| 0.8% Tween 80 | 0.00<br>98.78 [100.00] | A↓ | 0.00<br>102.42 [100.00] | A↓ |
| 5% solutions in DMSO, 1 day at room temperature | | | | |
| 1:100 dilution in pH 6.8 buffer | 0.00<br>96.98 [100.00] | A↓ | 0.00<br>101.85 [100.00] | A↓ |
| Solid state, 1 week 80° C., tight container | | | | |
| Bulk (HPLC) | 0.00<br>99.77 [100.00] | A | 0.00<br>100.77 [100.00] | A |
| Bulk (XRPD) | No change | | No change | |
| 30% in mixture 1 | 0.00<br>100.11 [100.00] | A | 0.00<br>101.23 [100.00] | A |
| 30% in mixture 2 | 2.17<br>94.28 [97.75] | A | 2.08<br>93.43 [97.82] | A |
| Solid state, 1 week 80° C., 75% relative humidity | | | | |
| Bulk (HPLC) | 0.00<br>99.97 [100.00] | A | 0.00<br>100.71 [100.00] | A |
| Bulk (XRPD) | No change | | No change | |
| 30% in mixture 1 | 0.00<br>99.38 [100.00] | B | 0.00<br>100.88 [100.00] | B |
| 30% in mixture 2 | 3.71<br>89.37 [96.02] | B | 1.89<br>92.17 [97.99] | B |
| Xenon light (approximately 1200 kLuxh) | | | | |
| Bulk (HPLC) | 0.00<br>96.03 [100.00] | A | 0.00<br>99.73 [100.00] | A |
| Bulk (XRPD) | No change | | No change | |
| Bulk corrosivity | | | | |
| 2 day, 80% relative humidity with steel coupon | N/A | | No change | |

↓ suspension
A no change of color
*clear solution after stress test
B slight discoloration Mixture 1: 30% 4-methyl-N-[3-(4-methyl-imidazol-1-yl)-5-trifluoromethyl-phenyl]-3-(4-pyridin-3-yl-pyrimidin-2-ylamino)-benzamide (free base or salt), 63% lactose 100 mesh/lactose 200 mesh (50:50), 5% crosprovidone, 1% Aerosil 200, 1% magnesium stearate Mixture 2: 30% 4-methyl-N-[3-(4-methyl-imidazol-1-yl)-5-trifluoromethyl-phenyl]-3-(4-pyridin-3-yl-pyrimidin-2-ylamino)-benzamide (free base or salt), 34% mannitol 60, 34% Avicel PH102, 1% Aerosil 200, 1% magnesium stearate (% by weight of free base or salt)

TABLE 16

Forced Decomposition Test

| Test condition | Appearance | Degradation products | Assay [% area] |
|---|---|---|---|
| Unstressed | | 0.00 (0) | 99.22 [100.00] |
| Bulk 3 days/100° C. | A | 0.00 (0) | 99.02 [100.00] |
| 10 mg/1.5 mL DMSO + 0.5 mL water 3 days/100° C. | A* | 0.75 (4) | 97.04 [99.24] |
| 10 mg/1.5 mL DMSO + 0.5 mL 0.1 N HCl 3 days/50° C. | A* | 11.64 (7) | 89.15 [88.45] |
| | A* | 0.00 (0) | 100.04 [100.00] |
| 10 mg/1.5 mL DMSO + 0.5 mL 0.1N NaOH 3 days/50° C. | A* | 6.79 (3) | 94.64 [93.30] |
| 10 mg/1.5 mL DMSO + 0.5 mL water containing 200 ppm $Fe^{3+}$, $Ni^{2+}$ and $Cu^{2+}$ saturated with $O_2$ 3 days/100° C. | A* | 1.66 (5) | 96.89 [98.32] |
| 10 mg/1.5 mL DMSO + 0.5 mL water saturated with $O_2$ 3 days/100° C. | A* | 0.58 (2) | 99.37 [99.42] |
| 10 mg/1.5 mL DMSO + 0.5 mL 10% $H_2O_2$ 3 days/100° C. | B* | 0.34 (2) | 98.85 [99.66] |
| 10 mg/1.5 mL DMSO + 0.5 mL water xenon light (1200 kLux) | B* | 2.74 (5) | 96.10 [97.23] |

TABLE 17

Chemical and Physicochemical Characteristics

| | Salt form | | | |
|---|---|---|---|---|
| | Free base form B | | Hydrochloride monohydrate (form B) | |
| Parameter | Calculated | Found | Calculated | Found |
| Elementary analysis | | | | |
| % C | 63.46 | 63.58 | 57.58 | 57.66 |
| % H | 4.15 | 3.97 | 4.29 | 4.25 |
| % F | 10.76 | 10.22 | 9.77 | 9.83 |
| % N | 18.51 | 18.57 | 16.80 | 16.58 |
| % O | 3.02 | 3.56 | 5.48 | 5.68 |
| % Cl | N/A | N/A | 6.08 | 6.00 |
| DSC purity (mol %) (10° C./minute) | 98.65 | | N/A due to decomposition prior to melting | |
| HPLC purity (area %) | 100.00 | | 100.00 | |
| DSC melting point (° C.) (10° C./minute) | 249.0 | | N/A due to decomposition prior to melting | |
| Melting enthalpy (J/g) | 153.9 | | N/A due to decomposition prior to melting | |
| pH of 1% solution or suspension in water | 7.99 | | 2.53 | |
| Solubility (approximately at 25° C., mg/mL) | | | | |
| 0.1N HCl | 0.60 | | 0.94 | |
| 0.01N HCl | 0.0014 | | 0.08 | |
| Phosphate buffer, pH 6.8 | 0.0002 | | Below detection | |
| Water | Below detection | | 0.17 | |
| Ethanol | 0.63 | | 3.69 | |
| Isopropanol | 0.33 | | 1.93 | |
| Thermogravimetry (weight loss %) (10° C./minute) | 0.026 (RT to 200° C.) | | 0.91 (RT to 80° C.) | |
| Residual solvents (%) | 0.2 | | 0.0 | |
| Intrinsic dissolution rate (mg $min^{-1}cm^{-2}$) | | | | |
| pH 1 (0.1N HCl) | 0.17 | | 0.17 | |
| Water | 0.0013 | | 0.0024 | |

The chemical, physicochemical and morphic characteristics of both 4-methyl-N-[3-(4-methyl-imidazol-1-yl)-5-trifluoromethyl-phenyl]-3-(4-pyridin-3-yl-pyrimidin-2-ylamino)-benzamide free base (form B) and 4-methyl-N-[3-(4-methyl-imidazol-1-yl)-5-trifluoromethyl-phenyl]-3-(4-pyridin-3-yl-pyrimidin-2-ylamino)-benzamide monohydrate hydrochloride salt (form B) were evaluated as described below.

Determination of Approximate Solubility: A weighted amount (20-50 mg) of sample was charged into 2 mL of the solvent. The obtained slurry was allowed to equilibrate for 24 hours at room temperature and then filtered. The concentration of DS in saturated filtrate was measured by either UV or HPLC.

Intrinsic Dissolution Rate (IDR): Dissolution rate measurements were performed at 37° C. using the rotating disk method (VanKell Instrument). A single rotation speed of 200 rpm was used. For IDR in 0.1 N HCl, an 800 mL volume, and for IDR in water, a 200 mL volume were used. The solution was continuously pumped through a UV measuring cell and recycled to the dissolution vessel.

Hygroscopicity: Sorption/desorption isotherms were collected using a Surface Measurements Systems dynamic vapor sorption device (DVS-1). The measurements were carried out at 25° C.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A method of treating chronic myelogenous leukemia comprising the step of administering to a subject in need thereof, a therapeutically effective amount of a salt, 4-methyl-N-[3-(4-methyl-imidazol-1-yl)-5-trifluoromethyl-phenyl]-3-(4-pyridin-3-yl-pyrimidin-2-ylamino)-benzeneamide monohydrochloride monohydrate.

2. A method of treating chronic myelogenous leukemia comprising the step of administering to a subject in need thereof, a therapeutically effective amount of a pharmaceutical composition comprising: a therapeutically effective amount of a salt, 4-methyl-N-[3-(4-methyl-imidazol-1-yl)-5-trifluoromethyl-phenyl]-3-(4-pyridin-3-yl-pyrimidin-2-ylamino)-benzeneamide monohydrochloride monohydrate and at least one pharmaceutically acceptable carrier, diluent, vehicle or excipient.

* * * * *